US012806372B2

(12) United States Patent
Scherich et al.

(10) Patent No.: US 12,806,372 B2
(45) Date of Patent: Nov. 24, 2026

(54) CONCENTRIC CATHETERS AND RELATED SYSTEMS AND METHODS

(71) Applicant: Becton, Dickinson and Company, Franklin Lakes, NJ (US)

(72) Inventors: Megan Scherich, Salt Lake City, UT (US); Jonathan Karl Burkholz, Salt Lake City, UT (US); Weston F. Harding, Lehi, UT (US); Benjamin Hopwood, Salt Lake City, UT (US); Curtis H. Blanchard, Riverton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 284 days.

(21) Appl. No.: 17/339,532

(22) Filed: Jun. 4, 2021

(65) Prior Publication Data

US 2021/0402141 A1 Dec. 30, 2021

Related U.S. Application Data

(60) Provisional application No. 63/045,571, filed on Jun. 29, 2020.

(51) Int. Cl.
*A61M 25/00* (2006.01)
*A61M 25/09* (2006.01)

(52) U.S. Cl.
CPC .... *A61M 25/0051* (2013.01); *A61M 25/0067* (2013.01); *A61M 25/09* (2013.01); *A61M 2025/0004* (2013.01)

(58) Field of Classification Search
CPC .. A61M 2025/0004; A61M 2025/0039; A61M 2025/0681; A61M 2025/0175; A61M 25/0606; A61M 25/0017; A61M 25/0693; A61M 25/0075; A61M 25/0113; A61M 25/0097; A61M 25/0631; A61M 25/0662; A61M 25/0026; A61M 39/10;
(Continued)

(56) References Cited

U.S. PATENT DOCUMENTS 5,201,712 A 4/1993 Bryant
6,236,876 B1 5/2001 Gruner et al.
(Continued)

FOREIGN PATENT DOCUMENTS

BR PI1008373 B1 10/2019
CN 101355912 A 1/2009
(Continued)

*Primary Examiner* — Michael J Tsai
*Assistant Examiner* — Kathleen Paige Vokes
(74) *Attorney, Agent, or Firm* — The Webb Law Firm

(57) ABSTRACT

A catheter system may include an outer catheter adapter, an outer catheter having an outer catheter lumen extending through the outer catheter, and an inner surface forming the outer catheter lumen. The catheter system may further include an inner catheter adapter, an inner catheter lumen extending through the inner catheter adapter and an inner catheter extending distally from the inner catheter adapter such that the inner catheter is disposed within the outer catheter lumen and the inner catheter and the inner catheter adapter are configured to move with respect to the outer catheter and the outer catheter adapter between a proximal position and a distal position.

13 Claims, 8 Drawing Sheets

(58) Field of Classification Search

CPC ........ A61M 25/0136; A61M 25/09041; A61M 2005/3246; A61M 5/3243; A61M 2005/3256; A61M 2005/3268; A61M 5/3275; A61M 2039/1077; A61M 25/0637; A61M 25/065; A61M 2025/09116; A61M 25/0014; A61B 1/00142; A61B 1/00154; A61B 1/015; A61B 5/1405; A61B 2017/00991; A61B 17/3421; A61B 1/0052; A61B 1/0055; A61B 1/00133; A61B 17/3417; A61B 2017/00367; A61B 2017/00407; A61B 5/15003; A61B 5/150992

See application file for complete search history.

(56) References Cited

U.S. PATENT DOCUMENTS

| | | | | |
|---|---|---|---|---|
| 8,740,859 | B2 | 6/2014 | McKinnon et al. | |
| 10,010,392 | B1 | 7/2018 | Zukowski | |
| 2004/0044318 | A1* | 3/2004 | Fiser et al. | A61M 5/3275 |
| 2005/0059931 | A1 | 3/2005 | Garrison et al. | |
| 2007/0055327 | A1* | 3/2007 | Esch et al. | A61B 18/082 |
| 2008/0319387 | A1 | 12/2008 | Amisar et al. | |
| 2009/0024084 | A1* | 1/2009 | Khosla et al. | A61M 25/0097 |
| 2010/0204648 | A1 | 8/2010 | Stout et al. | |
| 2010/0210934 | A1* | 8/2010 | Belson | A61B 5/150503 |
| 2012/0078095 | A1* | 3/2012 | Heck | A61M 25/0606 |
| 2012/0143123 | A1 | 6/2012 | Agnew | |
| 2012/0179144 | A1 | 7/2012 | Carleo | |
| 2013/0110083 | A1 | 5/2013 | Koehler | |
| 2013/0274673 | A1* | 10/2013 | Fischell et al. | A61M 25/0084 |
| 2013/0274711 | A1 | 10/2013 | O'Day | |
| 2014/0171941 | A1 | 6/2014 | Thompson et al. | |
| 2015/0151088 | A1 | 6/2015 | Lim et al. | |
| 2017/0086802 | A1* | 3/2017 | Mamiya et al. | A61B 1/009 |
| 2017/0303890 | A1* | 10/2017 | Yamashita | B29C 66/5227 |
| 2018/0161541 | A1* | 6/2018 | Haldis et al. | A61M 25/0026 |
| 2018/0339131 | A1* | 11/2018 | Muse et al. | A61M 25/0068 |
| 2019/0069973 | A1* | 3/2019 | Isaacson et al. | A61M 25/0074 |
| 2019/0133564 | A1 | 5/2019 | Kirkemo | |
| 2019/0151607 | A9 | 5/2019 | O'Connell et al. | |
| 2019/0183641 | A1 | 6/2019 | Ganesan et al. | |
| 2019/0275303 | A1* | 9/2019 | Tran et al. | A61M 25/09041 |
| 2020/0094025 | A1* | 3/2020 | Wisman | A61M 29/00 |
| 2020/0100716 | A1* | 4/2020 | Devgon et al. | A61M 25/0113 |
| 2020/0230368 | A1* | 7/2020 | Breindel et al. | A61M 25/0631 |

FOREIGN PATENT DOCUMENTS

| | | | |
|---|---|---|---|
| CN | 201208419 | Y | 3/2009 |
| CN | 209347891 | U | 9/2019 |
| CN | 215900672 | U | 2/2022 |
| JP | 2009504203 | A | 2/2009 |
| WO | 2009049823 | A1 | 4/2009 |

* cited by examiner

CONCENTRIC CATHETERS AND RELATED SYSTEMS AND METHODS

RELATED APPLICATIONS

This application claims benefit of U.S. Provisional Patent Application No. 63/045,571, filed on Jun. 29, 2020, entitled CONCENTRIC CATHETERS AND RELATED SYSTEMS AND METHODS, which is incorporated herein in its entirety.

BACKGROUND

A catheter is commonly used to infuse fluids into vasculature of a patient. For example, the catheter may be used for infusing normal saline solution, various medicaments, or total parenteral nutrition. The catheter may also be used for withdrawing blood from the patient.

The catheter may include an over-the-needle peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and the introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using the catheter may be difficult for several reasons, particularly when a dwell time of the catheter within the vasculature is more than one day. When the catheter is left inserted in the patient for a prolonged period of time, the catheter or vein may be more susceptible to narrowing, collapse, kinking, blockage by debris (e.g., fibrin or platelet clots), and adhering of a tip of the catheter to the vasculature. Due to this, the catheter may become compromised for infusion, blood draw, or aspiration over time. The catheter is often used for acquiring a blood sample at a time of catheter placement, but the catheter is less frequently used for acquiring a blood sample during the catheter dwell period. Therefore, when a blood sample is required, an additional needle stick is often used to provide vein access for blood collection, which may be painful for the patient and result in higher material costs.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems and related devices and methods. In some embodiments, a catheter system may facilitate aspirations, blood draw, and infusions by opening a fluid path through the catheter system while also reducing a risk of microbial ingress and dislodgement of the catheter system from vasculature of a patient. In some embodiments, the catheter system may include an outer catheter adapter, which may include a distal end and a proximal end. In some embodiments, the catheter system may include an outer catheter, which may include a distal end, a proximal end, an outer catheter lumen extending through the distal end of the outer catheter and the proximal end of the outer catheter, and an inner surface forming the outer catheter lumen. In some embodiments, the outer catheter may extend distally from the distal end of the outer catheter adapter, and the distal end of the outer catheter may include a distal opening.

In some embodiments, the catheter system may include an inner catheter adapter, which may include a distal end, a proximal end, and an inner catheter lumen extending through the distal end of the inner catheter adapter and the proximal end of the inner catheter adapter. In some embodiments, the inner catheter and the outer catheter may be concentric. In some embodiments, the inner catheter may extend distally from the distal end of the inner catheter adapter, and the inner catheter may be disposed within the outer catheter lumen. In some embodiments, the inner catheter and the inner catheter adapter may be configured to move with respect to the outer catheter and the outer catheter adapter between a proximal position and a distal position. In some embodiments, in response to the inner catheter and the inner catheter adapter being in the distal position, the distal end of the inner catheter may be disposed distal to the distal end of the outer catheter.

In some embodiments, the catheter system may include a gap disposed between an outer surface of the inner catheter and the inner surface of the outer catheter. In some embodiments, in response to the inner catheter and the inner catheter adapter being in the distal position, the inner catheter may be disposed within the distal opening to restrict flow distally into the gap. In some embodiments, in response to movement of the inner catheter from the distal position to the proximal position, the inner catheter may be disposed proximal to the distal opening and the gap may be in fluid communication with the distal opening.

In some embodiments, the inner catheter adapter may be slidable relative to outer catheter adapter to move the inner catheter adapter and the inner catheter between the proximal position and the distal position. In some embodiments, the catheter system may include a toggle joint, which may include a distal end coupled to the outer catheter adapter and a proximal end coupled to the inner catheter adapter. In some embodiments, the toggle joint may be configured to depress to move the inner catheter and the inner catheter adapter to the proximal position.

In some embodiments, the inner catheter and the inner catheter adapter may be configured to move with respect to the outer catheter and the outer catheter adapter between a first position and a second position. In some embodiments, the catheter system may include multiple fenestrations disposed within the outer catheter or the inner catheter. In some embodiments, the fenestrations may be blocked when the inner catheter is in the first position. In some embodiments, in response to movement of the inner catheter from the first position to the second position, the fenestrations may be unblocked to allow fluid to flow through the fenestrations into the inner catheter lumen.

In some embodiments, the fenestrations may be disposed within the outer catheter, and the catheter system may include multiple other fenestrations disposed within the inner catheter. In some embodiments, the inner catheter and the inner catheter adapter may be configured to rotate with respect to the outer catheter and the outer catheter adapter between the first position and the second position. In some embodiments, in response to the inner catheter and the inner catheter adapter being in the second position, the fenestrations and the other fenestrations may be aligned. In some embodiments, in response to the inner catheter and the inner catheter adapter being in the first position, the fenestrations and the other fenestrations may be misaligned.

In some embodiments, the inner catheter and the inner catheter adapter may be configured to slide with respect to the outer catheter and the outer catheter adapter between the first position and the second position. In some embodiments, in response to the inner catheter being in the second position, the inner catheter may extend through the distal opening of the outer catheter. In some embodiments, the fenestrations may be disposed within the distal end of the inner catheter. In these and other embodiments, the fenestrations may be disposed distal to the distal opening of the outer catheter in response to movement of the inner catheter from the first position to the second position.

In some embodiments, the fenestrations may be disposed within the outer catheter, and the other fenestrations may be disposed within the inner catheter. In these and other embodiments, in response to the inner catheter and the inner catheter adapter being in the second position, the fenestrations and the other fenestrations may be aligned, and in response to the inner catheter and the inner catheter adapter being in the first position, the fenestrations and the other fenestrations may be misaligned. In some embodiments, the fenestrations may be disposed within the distal end of the outer catheter or within the proximal end of the outer catheter.

In some embodiments, the inner catheter and the inner catheter adapter may be configured to slide with respect to the outer catheter and the outer catheter adapter between the first position and the second position. In these and other embodiments, the fenestrations may be disposed within the outer catheter, and in response to the inner catheter moving between the first position and the second position, the distal end of the inner catheter may move distal to the fenestrations.

In some embodiments, the catheter may include multiple fenestrations within the wall. In some embodiments, the catheter system may include a tube disposed within the catheter. In some embodiments, the tube may include a distal end and may be configured to move between a proximal position and a distal position. In some embodiments, in response to the tube moving between the proximal position and the distal position, the distal end of the tube may move distal to the fenestrations of the catheter.

In some embodiments, the distal end of the tube may include a sharp edge. In some embodiments, a proximal end of the tube may be coupled to a guidewire. In some embodiments, the catheter system may include an outer catheter, and the catheter may be an inner catheter disposed within the outer catheter. In these and other embodiments, the tube may be disposed within the inner catheter lumen. In some embodiments, the catheter system may include the toggle joint, which may include the distal end of the toggle joint coupled to the catheter adapter and the proximal end of the toggle joint coupled to the tube. In some embodiments, the toggle joint may be configured to depress to move the tube to the proximal position.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DETAILED DESCRIPTION

As used in the present disclosure, the term "distal" refers to a direction away from a clinician who would place the device into contact with a patient, and nearer to the patient. As used in the present disclosure, the term "proximal" refers to a direction nearer to the clinician who would place the device into contact with the patient, and farther away from the patient.

Figure 1A:
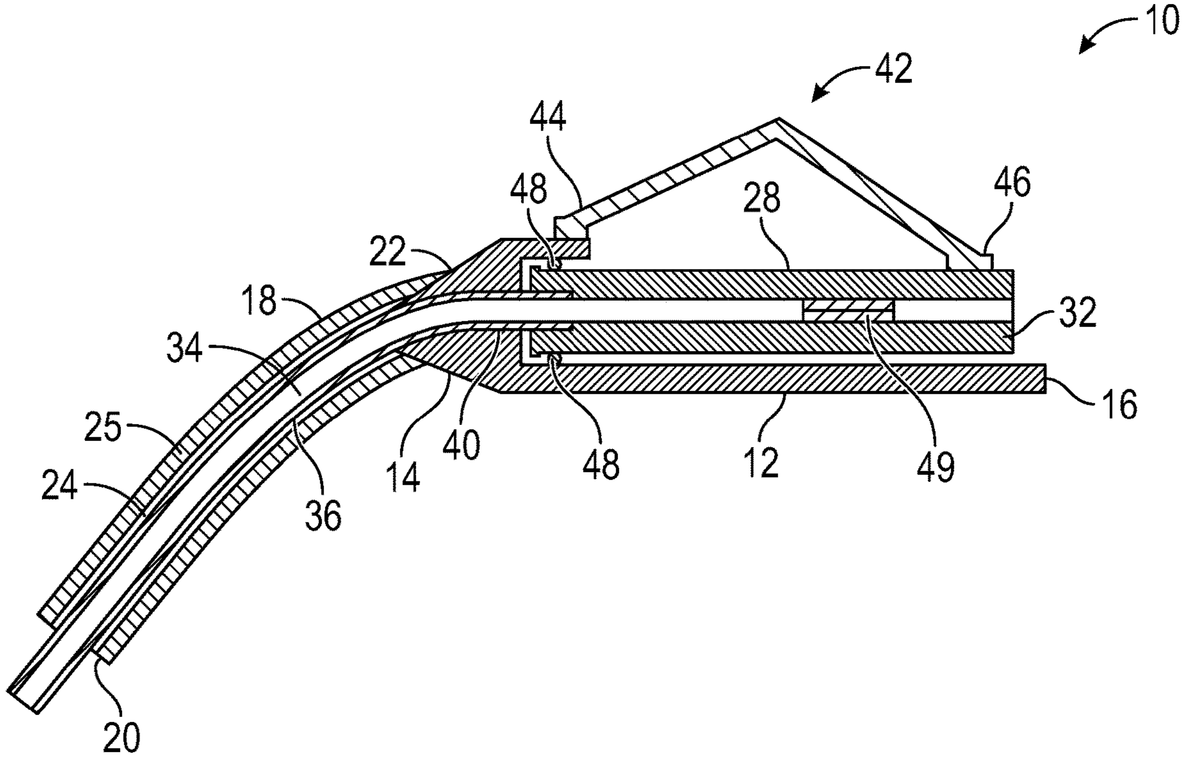
FIG. 1A is a cross-sectional view of an example catheter system, illustrating an example inner catheter and an example inner catheter adapter in an example distal position, according to some embodiments.
Figure 1B:
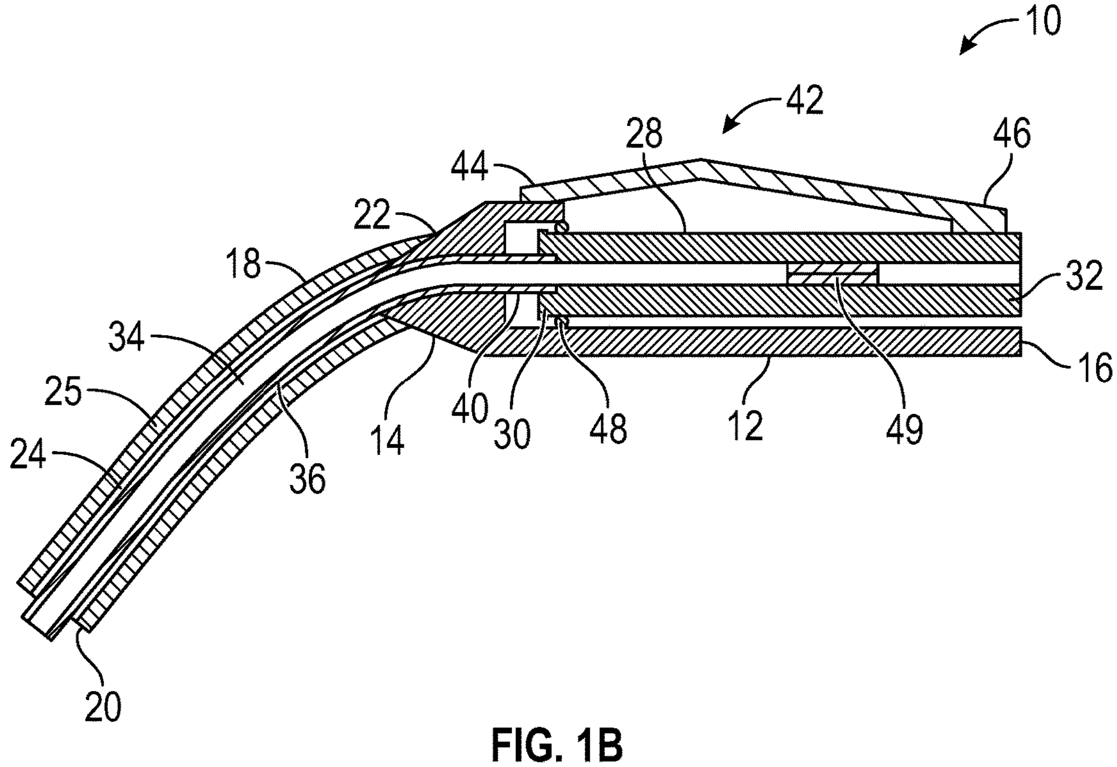
FIG. 1B is a cross-sectional view of the catheter system, illustrating the inner catheter and the inner catheter adapter in an example proximal position, according to some embodiments.

Referring now to FIGS. 1A-1B, in some embodiments, the catheter system 10 may include an outer catheter adapter 12, which may include a distal end 14 and a proximal end 16. In some embodiments, the catheter system 10 may include an outer catheter 18 which may include a distal end 20, a proximal end 22, an outer catheter lumen 24 extending through the distal end 20 of the outer catheter 18 and the proximal end 22 of the outer catheter 18, and an inner surface 25 forming the outer catheter lumen 24. In some embodiments, the outer catheter 18 may extend distally from the distal end 14 of the outer catheter adapter 12. In some embodiments, the distal end 20 of the outer catheter may include a distal opening 26.

In some embodiments, the catheter system 10 may further include an inner catheter adapter 28. In some embodiments, the inner catheter adapter 28 may include a distal end 30, a proximal end 32, and an inner catheter lumen 34 extending through a distal end 30 of the inner catheter adapter 28 and the proximal end 32 of the inner catheter adapter 28. In some embodiments, an inner catheter 36 may extend distally from the distal end 30 of the inner catheter adapter 28. In some embodiments, the inner catheter 36 may be disposed within the outer catheter lumen 24. In some embodiments, the inner catheter 36 and the inner catheter adapter 28 may be configured to move with respect to the outer catheter 18 and the outer catheter adapter 12 between a distal position, illustrated, for example, in FIG. 1A, and a proximal position, illustrated, for example, in FIG. 1B.

In some embodiments, in response to the inner catheter 36 and the inner catheter adapter 28 being in the proximal position, as illustrated, for example, in FIG. 1B, a distal end 38 of the inner catheter 36 may be disposed distal to the distal end 20 of the outer catheter 18. In some embodiments, in response to the inner catheter 36 and the inner catheter adapter 28 being in the distal position, as illustrated, for example, in FIG. 1A, the distal end 38 of the inner catheter 36 may be disposed more distal to the distal end 20 of the outer catheter 18 than in the proximal position.

In some embodiments, the outer catheter 18 may be coupled to the outer catheter adapter 12 via an interference fit, a bushing, an adhesive, or another suitable technique or device. In some embodiments, the inner catheter 36 may be coupled to the inner catheter adapter 28 via an interference fit, a bushing, an adhesive, or another suitable technique or device.

In some embodiments, the inner catheter adapter 28 may be slidable relative to the outer catheter adapter 12 to move the inner catheter adapter 28 and the inner catheter 36 between the proximal position and the distal position. In some embodiments, the outer catheter 18 may be stationary within vasculature of a patient when the inner catheter 36 is moved, and thus, not dislodged from the vasculature in response to movement of the inner catheter 36.

In some embodiments, the catheter system 10 may include a toggle joint 42 to facilitate moving or sliding the inner catheter adapter 28 relative to the outer catheter adapter 12, thereby moving or sliding the inner catheter 36 relative to the outer catheter 18. In some embodiments, the toggle joint 42 may also reduce a risk of bacterial contamination by allowing the user to contact the toggle joint 42 instead of a particular catheter adapter to move the inner catheter 36 within the vasculature.

In some embodiment, the toggle joint 42 may include a distal end 44 coupled to the outer catheter adapter 12 and a proximal end 46 coupled to the inner catheter adapter 28. In some embodiments, the toggle joint 42 may be configured to depress to move the inner catheter 36 and the inner catheter adapter 28 to the proximal position. In some embodiments, the toggle joint 42 may be depressed from a first position, illustrated, for example, in FIG. 1A, to a second position, illustrated, for example, in FIG. 1B. In some embodiments, the toggle joint 42 may be more angled in the first position than the second position. In some embodiments, the toggle joint 42 may be generally straight in the second position. In some embodiments, in response to toggle no longer being depressed, the toggle joint 42 may remain in the second position or the toggle joint 42 may return to the first position, which may move the inner catheter 36 and the inner catheter adapter 28 to the distal position.

In some embodiments, the toggle joint 42 may be constructed of a flexible polymer or other suitable material. In some embodiments, the toggle joint 42 may be configured to fold at a groove or crease between the distal end 44 and the proximal end 46. In some embodiments, the toggle joint 42 may be resilient. In some embodiments, the flexible polymer or other suitable material may facilitate folding at the groove. In some embodiments, the toggle joint 42 may be monolithically formed as a single unit. In other embodiments, the toggle joint 42 may include separate parts, which may be joined by one or more hinges.

In some embodiments, the inner catheter adapter 28 may be disposed within or on top of outer catheter adapter 12. In some embodiments, the outer catheter 18 may include an inner diameter greater than an outer diameter of the inner catheter 36 such that the outer catheter 18 may receive the inner catheter 36 therein.

In some embodiments, one or more seal elements 48, such as an O-ring, for example, may be disposed between the outer catheter adapter 12 and the inner catheter adapter 28 to seal a fluid path between the outer catheter adapter 12 and the inner catheter adapter 28. In some embodiments, the seal element 48 may include silicone, rubber, an elastomer, or another suitable material. In some embodiments, a lumen of the inner catheter adapter 28 may include a septum 49 to prevent blood from flowing through the proximal end 32 of the inner catheter adapter 28.

Figure 2A:
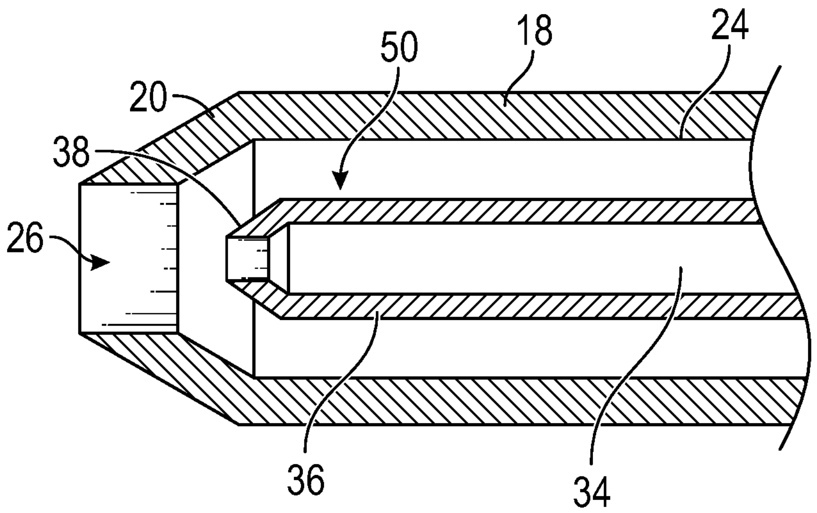
FIG. 2A is a cross-sectional view of a portion of the catheter system, illustrating the inner catheter and the inner catheter adapter in the proximal position and an example outer catheter, according to some embodiments.
Figure 2B:
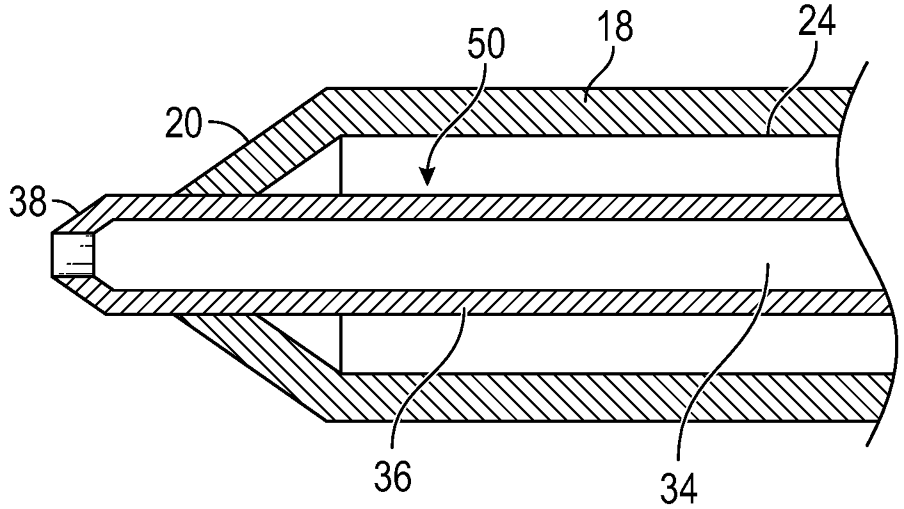
FIG. 2B is a cross-sectional view of a portion of the catheter system, illustrating the inner catheter and the inner catheter adapter in the distal position, according to some embodiments.

Referring now to FIGS. 2A-2B, the distal end 20 of the outer catheter 18 and the distal end 38 of the inner catheter 36 are illustrated, according to some embodiments. In some embodiments, the inner catheter adapter 28 may be moved in a proximal direction relative to the outer catheter adapter 12 to retract the inner catheter 36 or may be moved in a distal direction relative to the outer catheter adapter 12 to advance the inner catheter 36. In some embodiments, the toggle joint 42 (see FIGS. 1A-1B) may be used to move the inner catheter 36 as described with respect to FIGS. 1A-1B. In some embodiments, a screw-type adjuster as described, for example, with respect to FIG. 5, or another suitable mechanism may be used to move the inner catheter 36.

In some embodiments, in response to the inner catheter 36 and the inner catheter adapter 28 being in the proximal position, as illustrated, for example, in FIG. 2A, the distal end 38 of the inner catheter 36 may be disposed proximal to the distal opening 26 of the outer catheter 18. In some embodiments, in response to the inner catheter 36 and the inner catheter adapter 28 being in the distal position, as illustrated, for example, in FIG. 2B, the distal end 38 of the inner catheter 36 may be disposed distal to the distal opening 26 of the outer catheter 18.

In some embodiments, a gap 50 may be disposed between an outer surface of the inner catheter 36 and an inner surface of the outer catheter 18. In some embodiments, in response to the inner catheter 36 and the inner catheter adapter 28 being in the distal position and/or the proximal position, the gap 50 may be in fluid communication with the distal opening 26 of the outer catheter 18 such that in response to the outer catheter 18 being inserted into a vein, blood may flow through the distal opening 26 of the outer catheter 18 and into the gap 50. In some embodiments, the gap 50 may be annular.

In some embodiments, in response to the inner catheter 36 and the inner catheter adapter 28 being in the distal position, the inner catheter 36 may be disposed within the distal opening 26 and restrict, partially or completely, flow distally into the gap 50. The distal position is illustrated in FIG. 2B, according to some embodiments. In some embodiments, in response to movement of the inner catheter 36 from the distal position to the proximal position, the inner catheter 36 may be disposed proximal to the distal opening 26 and the gap 50 may be in fluid communication with the distal opening 26. The proximal position is illustrated in FIG. 2A, according to some embodiments.

In some embodiments, the inner catheter 36 and/or the outer catheter 18 may include one or more fenestrations or holes, which may facilitate flow of fluid in or out. In some embodiments, a distal end of the inner catheter 36 may be closed, which may prevent occlusion. In some embodiments, the distal end of the inner catheter 36 may be rounded and/or lubricated to reduce a likelihood of damaging a vein.

In some embodiments, between therapies, contact between the distal opening 26 and the inner catheter 36 may reduce a risk of a clot or thrombus entering the gap 50. In some embodiments, the inner catheter 36 may be moved to the proximal position for blood collection and/or infusion. In some embodiments, the inner catheter 36 may move proximally with respect to the outer catheter 18 to the proximal position, which may facilitate aspirations, blood draws, and infusions by ensuring an open fluid path, while also reducing risk of dislodgement of the outer catheter 18, microbial contamination, or other complications.

Figure 3:
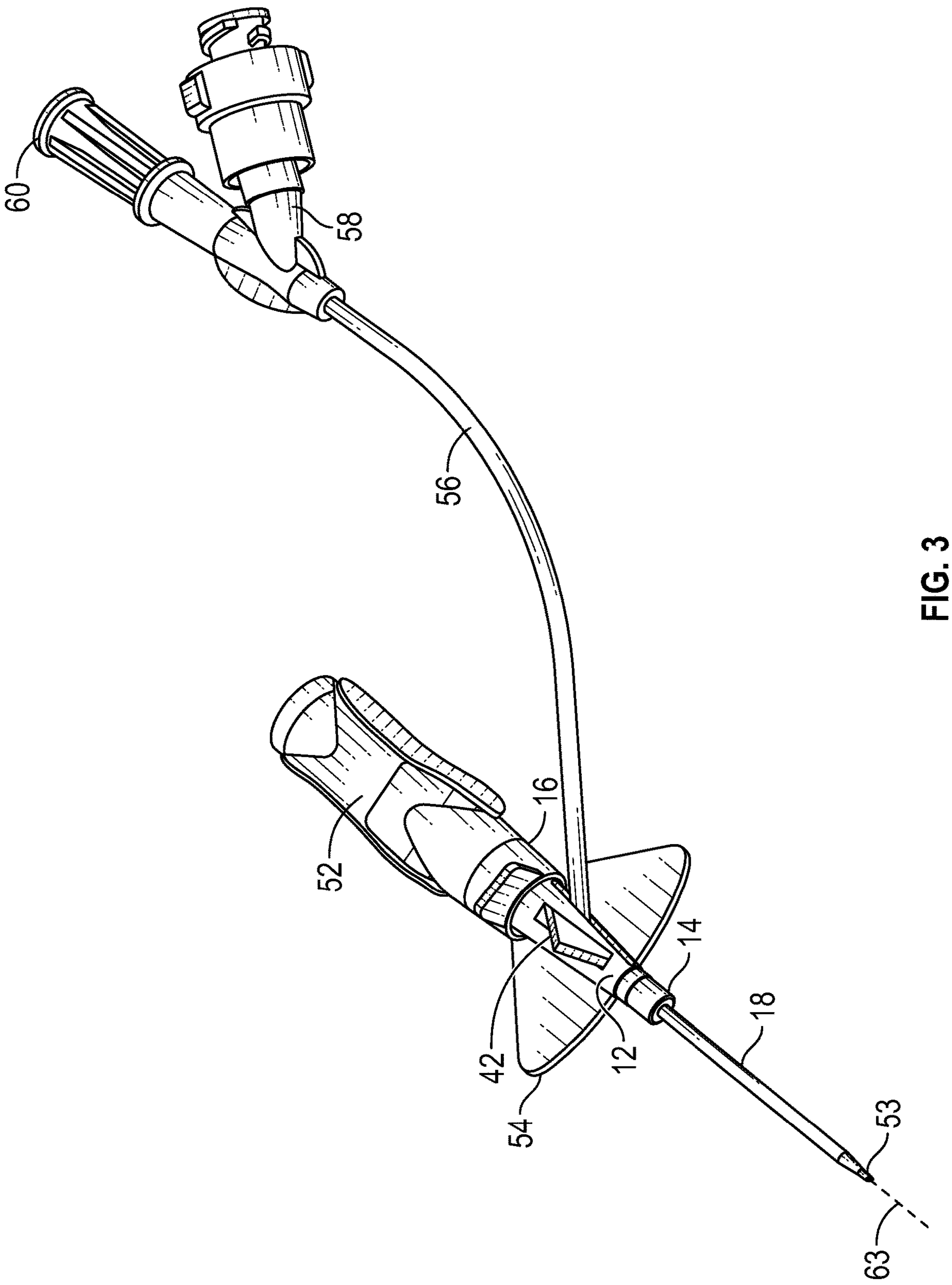
FIG. 3 is an upper perspective view of the catheter system, illustrating an example toggle joint, according to some embodiments.

Referring now to FIG. 3, the catheter system 10 is illustrated, according to some embodiments. In some embodiments, the catheter system 10 may include a needle hub 52, which may be removably coupled to the outer catheter adapter 12. In some embodiments, an introducer needle 53 may be coupled to the needle hub 52 and may extend through the outer catheter 18 and the inner catheter 36. In some embodiments, the outer catheter adapter 12 may include wings 54.

In some embodiments, the catheter system 10 may include an extension tube 56, which may include a distal end coupled the inner catheter adapter 28 and in fluid communication with the inner catheter lumen 34. In some embodiments, an adapter 58 may be coupled to a proximal end of the extension tube 56. In some embodiments, a fluid infusion device may be coupled to the adapter 58 to deliver fluid to the patient via the inner catheter 36, which is inserted in the vein. In some embodiments, a blood collection device may be coupled to the adapter 58 to withdraw blood from the patient via the inner catheter 36, which may be inserted in the vein. In some embodiments, the extension tube 56 may extend through a slot of the outer catheter adapter 12. In some embodiments, the catheter system 10 may not include the extension tube 56.

In some embodiments, the catheter system 10 may be vented to observe blood flashback and facilitate proximal flow of blood. In some embodiments, the catheter system 10 may be vented in any suitable manner. For example, a vent plug 60 may be coupled to the adapter 58 during insertion of the outer catheter 18 into the patient. In some embodiments, the vent plug 60 may be permeable to air but not to blood. In some embodiments, the inner catheter 36, the inner catheter adapter 28, the extension tube 56, the adapter 58, and the vent plug 60 may be in fluid communication.

Figure 4B:
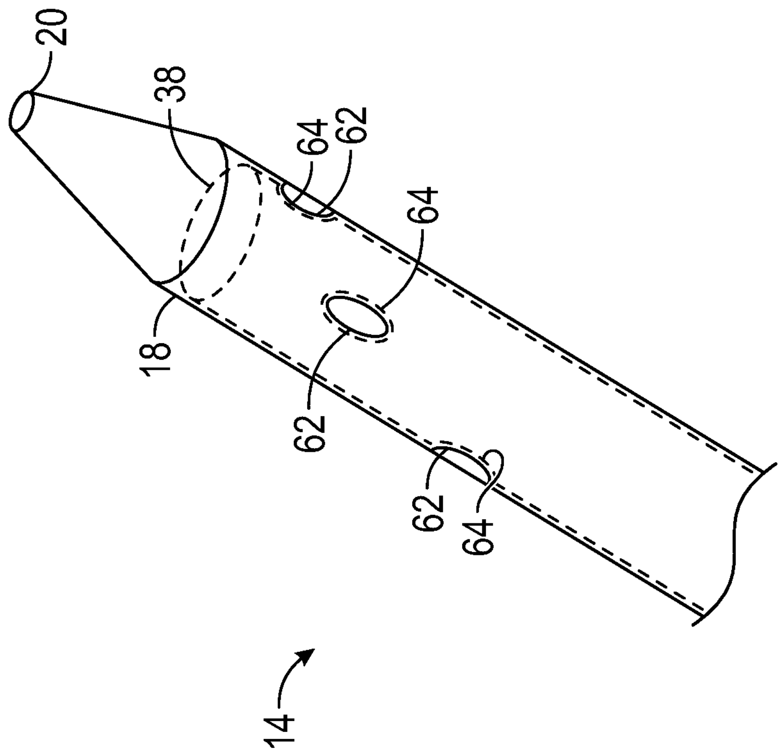
FIG. 4B is an upper perspective view of the inner catheter and the inner catheter adapter of FIG. 4A in the proximal position, illustrating the inner catheter in the distal position, according to some embodiments.
Figure 4A:
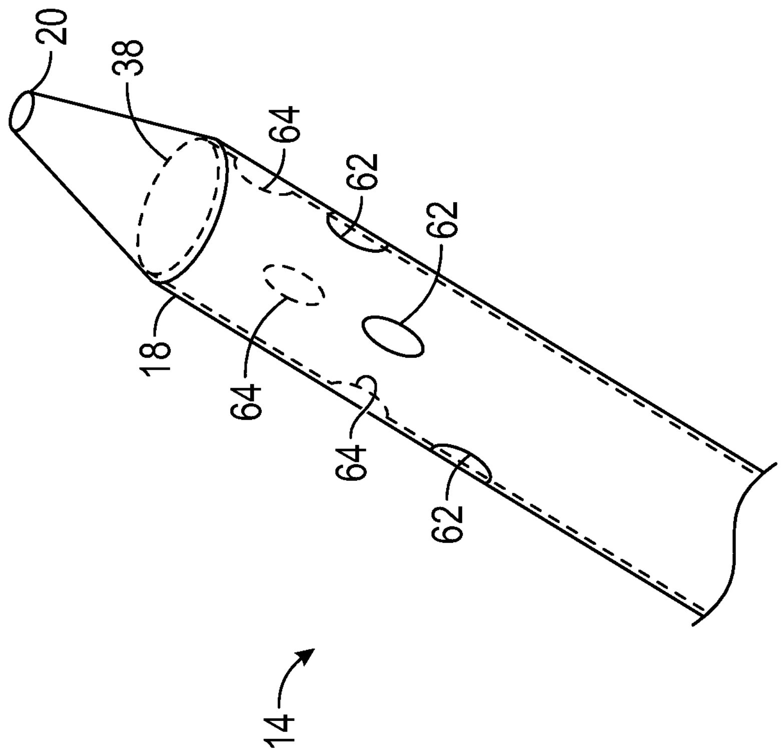
FIG. 4A is an upper perspective view of the inner catheter and the example inner catheter adapter in the distal position, illustrating example fenestrations, according to some embodiments.

Referring now to FIGS. 4A-4B, in some embodiments, the inner catheter 36 and the inner catheter adapter 28 may be configured to move with respect to the outer catheter 18 and the outer catheter adapter 12 between a first position, illustrated, for example, in FIG. 4A, and a second position, illustrated, for example, in FIG. 4B. In some embodiments, the first position and the second position may correspond to the distal position and the proximal position, respectively. In some embodiments, the toggle joint 42 (see FIGS. 1A-1B) may be used to move the inner catheter 36 as described with respect to FIGS. 1A-1B. In some embodiments, a screw-type adjuster as described, for example, with respect to FIG. 5, or another suitable mechanism may be used to move the inner catheter 36.

In some embodiments, one or more fenestrations 62 may be disposed within the outer catheter 18. In some embodiments, the fenestrations 62 may be disposed within the distal end 14 of the outer catheter 18. In some embodiments, the fenestrations 62 may be configured to be blocked by the inner catheter 36 when the inner catheter 36 is in the first position. In some embodiments, in response to movement of the inner catheter 36 from the first position to the second position, the fenestrations 62 may be unblocked to allow fluid to flow through the fenestrations 62 into the inner catheter lumen 34.

In some embodiments, the inner catheter 36 and the inner catheter adapter 28 may be configured to slide with respect to the outer catheter 18 and the outer catheter adapter 12 between the first position and the second position. In some embodiments, the inner catheter 36 and the inner catheter adapter 28 may be configured to slide with respect to the outer catheter 18 and the outer catheter adapter 12 along an axis 63 (see, for example, FIG. 3) aligned with the outer catheter 18.

In some embodiments, one or more other fenestrations 64 may be disposed within the inner catheter 36. In some embodiments, in response to the inner catheter 36 and the inner catheter adapter 28 being in the second position, the fenestrations 62 and the other fenestrations 64 may be aligned. In some embodiments, the other fenestrations 64 may be moved distally or proximally to align with the other fenestrations. Additionally or alternatively, the other fenestrations may be rotated to align with the other fenestrations.

In some embodiments, in response to the inner catheter 36 and the inner catheter adapter 28 being in the first position, the fenestrations 62 and the other fenestrations 64 may be misaligned. In some embodiments, the alignment of the fenestrations 62 and the other fenestrations 64 may increase flow of fluid through the inner catheter lumen 34, and misalignment of the fenestrations 62 and the other fenestrations 64 may prevent a thrombus or other obstruction from entering the inner catheter lumen 34. In some embodiments, an outer circumference of the inner catheter 36 may be slightly less than an inner circumference of the outer catheter 18 such that the inner catheter 36 may move with respect to the outer catheter 18 and/or fluid may not leak between the inner catheter 36 and the outer catheter 18. In some embodiments, the outer circumference of the inner catheter 36 may contact the inner circumference of the outer catheter 18 along all or a portion of the outer circumference.

Figure 4C:
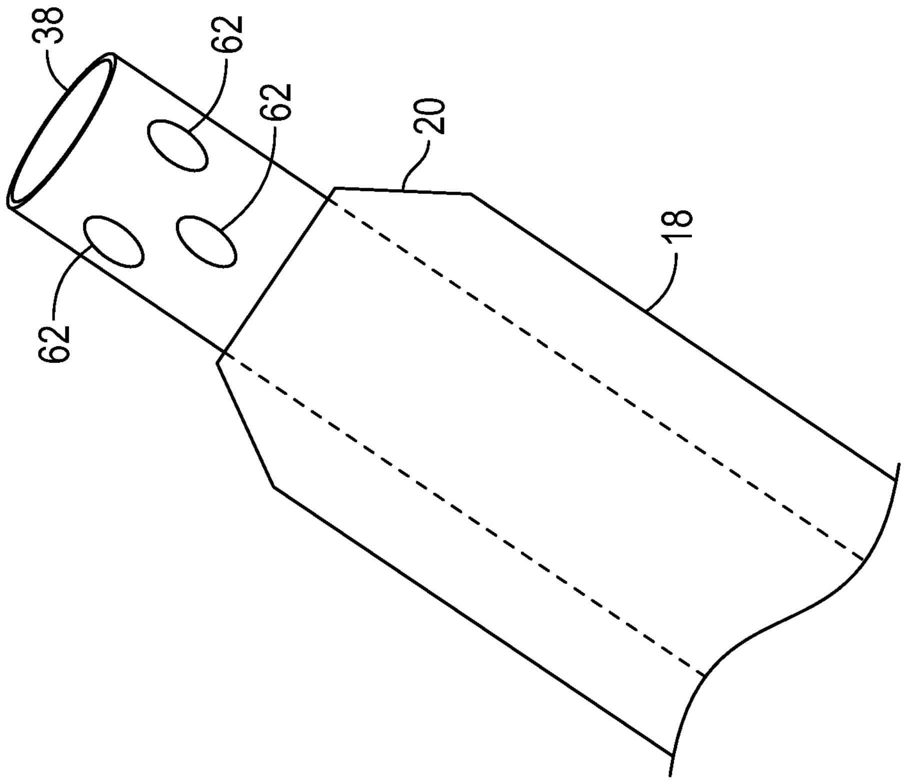
FIG. 4C is an upper perspective view of the inner catheter and the inner catheter adapter in the distal position, illustrating other example fenestrations, according to some embodiments.
Figure 4D:
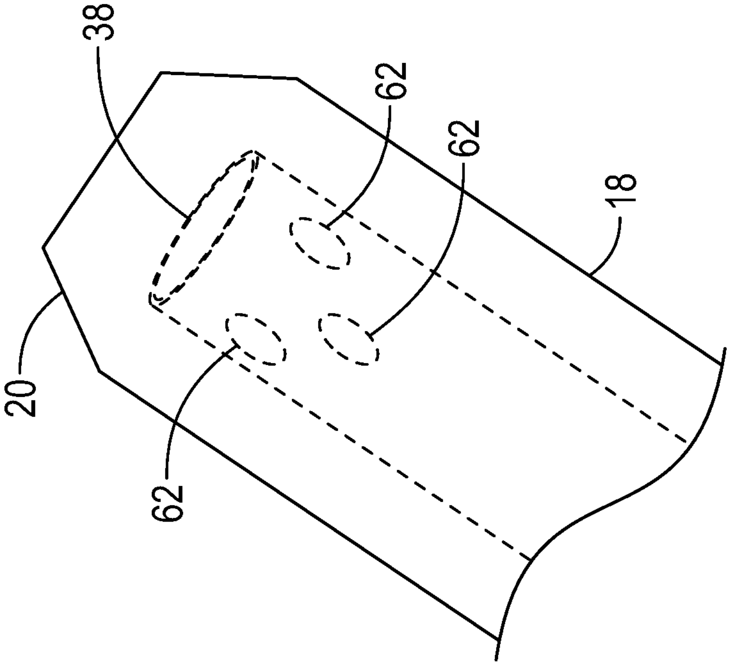
FIG. 4D is an upper perspective view of the inner catheter and the inner catheter adapter of FIG. 4C in the proximal position, according to some embodiments.

Referring now to FIGS. 4C-4D, in some embodiments, in response to the inner catheter 36 being in the second position, the inner catheter 36 may extend through the distal opening 26 of the outer catheter 18. In some embodiments, the distal end 38 of the inner catheter 36 may be open or closed. In some embodiments, the fenestrations 62 may be disposed within the distal end 38 of the inner catheter 36, and the fenestrations 62 may be disposed distal to the distal opening 26 of the outer catheter 18 in response to movement of the inner catheter 36 from the first position to the second position. In these embodiments, the fenestrations 62 may facilitate fluid flow through the fenestrations and into the inner catheter lumen 34 without including any fenestrations within the outer catheter 18.

In some embodiments, the toggle joint 42 (see FIGS. 1A-1B) may be used to move the inner catheter 36 as described with respect to FIGS. 1A-1B. In some embodiments, a screw-type adjuster as described, for example, with respect to FIG. 5, or another suitable mechanism may be used to move the inner catheter 36.

Figure 5:
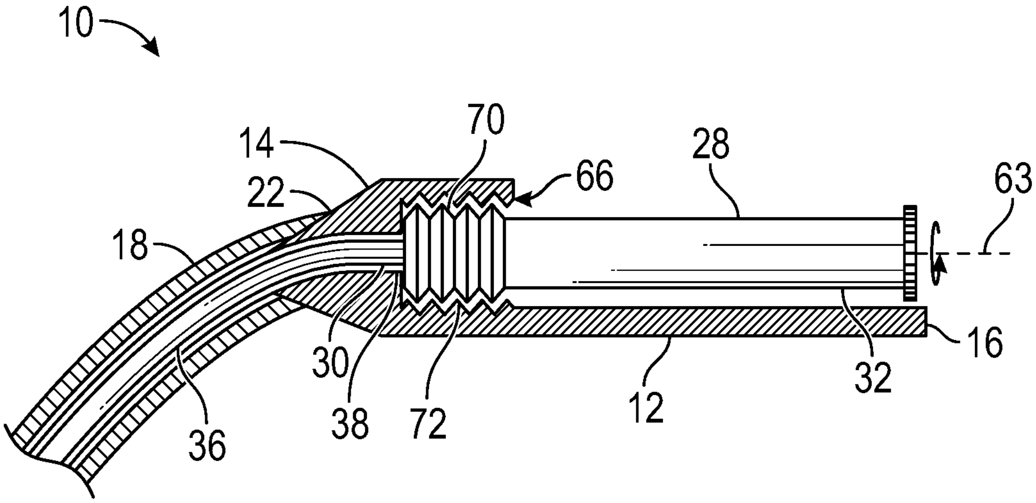
FIG. 5 is a partial cutaway view of the catheter system, illustrating example threading, according to some embodiments.

Referring now to FIG. 5, in some embodiments, the inner catheter 36 may be rotated with respect to the outer catheter 18 via a user-controlled method. For example, the catheter system 10 may include a screw-type adjustor 66. In some embodiments, the screw-type adjustor 66 may include threading 70, which may correspond to other threading 72. In some embodiments, the threading 70 may be disposed on an outer surface and/or the distal end 30 of the inner catheter adapter 28. In some embodiments, the other threading 72 may be disposed on an inner surface of the outer catheter adapter 12. In some embodiments, the inner catheter adapter 28 may be coupled to the outer catheter adapter 12 via the threading 70 and the other threading 72.

In some embodiments, the inner catheter adapter 28 and inner catheter 36 may rotate about the axis 63, which may be aligned with the outer catheter 18 between the first position and the second position. In further detail, the inner catheter adapter 28 may be threaded or unthreaded with respect to the outer catheter adapter 12 from the first position to the second position and/or from the second position to the first position. In some embodiments, the outer catheter adapter 12 may be stationary within the vasculature of the patient when the inner catheter 36 is moved, and thus, not dislodged from the vasculature in response to movement of the inner catheter 36.

Figure 6B:
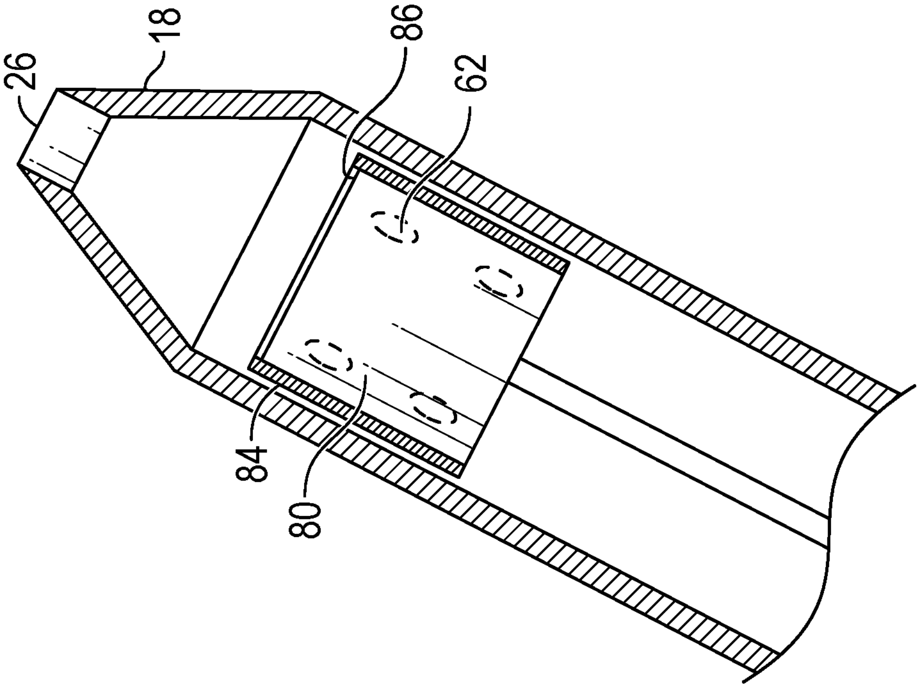
FIG. 6B is a cross-sectional view of a portion of the catheter system, illustrating the tube in a distal position, according to some embodiments.
Figure 6A:
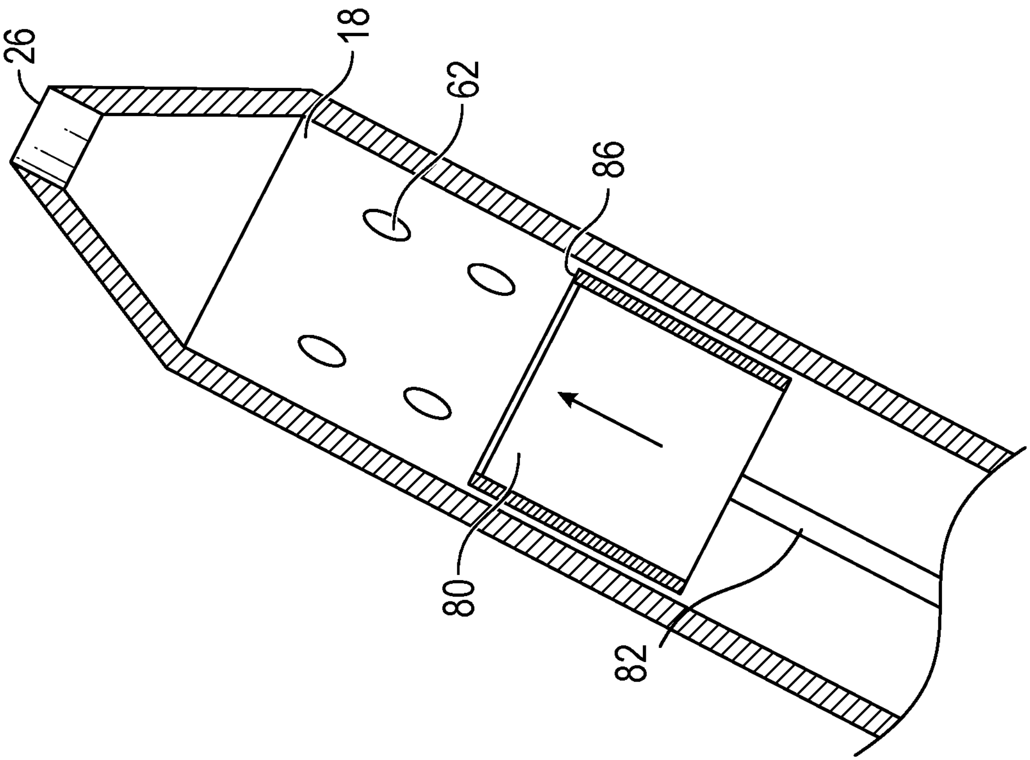
FIG. 6A is a cross-sectional view of a portion of the catheter system, illustrating an example tube in a proximal position, according to some embodiments.
Figure 6C:
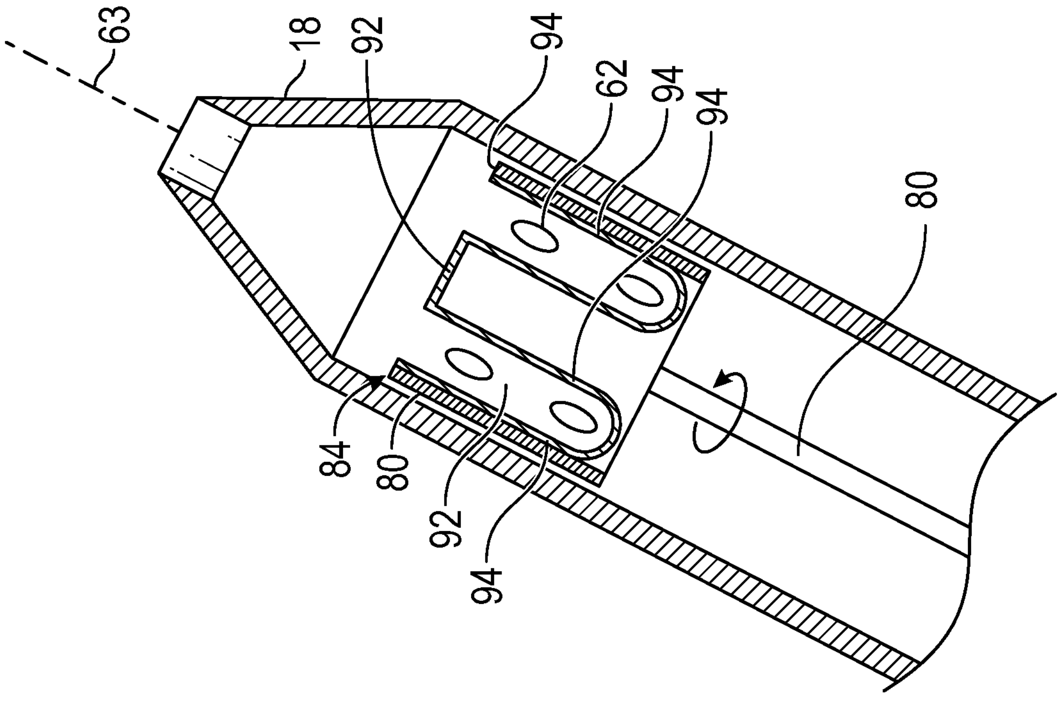
FIG. 6C is a cross-sectional view of a portion of the catheter system, illustrating the tube with one or more slots, according to some embodiments.

Referring now to FIGS. 6A-6C, in some embodiments, a tube 80 may be disposed within the outer catheter 18. In some embodiments, the tube 80 may correspond to the inner catheter 36. In other embodiments, the tube 80 may be coupled to a guidewire 82, which may be used to advance the tube 80 distally and/or retract the tube 80 proximally.

In some embodiments, the outer catheter 18 may include the fenestrations 62 through a wall of the outer catheter 18. In some embodiments, in response to the tube 80 moving between a proximal position, illustrated, for example, in FIG. 6A, and a distal position, illustrated, for example, in FIG. 6B, a distal end 84 of the tube 80 may contact and/or move distal to the fenestrations 62.

In some embodiments, a thrombus, clot or obstruction may block one or more of the fenestrations 62. In some embodiments, the distal end 84 of the tube 80 may cut or perforate the thrombus, clot, or obstruction to clear the fenestrations 104 and facilitate fluid flow there through. In some embodiments, the distal end 84 of the tube 80 may include a sharp edge 86. In some embodiments, the sharp edge 86 may be annular. In some embodiments, the sharp edge 86 may include metal, ceramic, high density polyethylene, or another suitable material. In some embodiments, the sharp edge 86 may clear the fenestrations with axial motion of the tube between the proximal position and the distal position (which may be accomplished by the user).

As illustrated in FIGS. 6C, in some embodiments, the tube 80 may include one or more slots 92, which may extend from the distal end 84 of the tube 80. In some embodiments, the slots 92 may include sharp edges 94, which may facilitate clearing the fenestrations 62 in response to the tube 80 and the guidewire 82 being rotated around the axis 63 (which may be accomplished by the user). In some embodiments, a width of each of the slots 92 may be greater than or equal to a width of the fenestrations 62.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:

an outer catheter adapter configured for placement external to a vasculature of a patient, the outer catheter adapter comprising a distal end and a proximal end;

an outer catheter, comprising a distal end configured for placement within the vasculature of the patient, a proximal end, an outer catheter lumen extending through the distal end of the outer catheter and the proximal end of the outer catheter, and an inner surface forming the outer catheter lumen, wherein the proximal end of the outer catheter is connected to the outer catheter adapter and extends distally from the distal end of the outer catheter adapter, and the distal end of the outer catheter comprises a distal opening;

an inner catheter adapter, comprising a distal end, a proximal end, and an inner catheter lumen extending through the distal end of the inner catheter adapter and to the proximal end of the inner catheter adapter;

an inner catheter comprising a distal end configured for placement within the vasculature, the inner catheter connected to the inner catheter lumen of the inner catheter adapter and extending distally from the distal end of the inner catheter adapter, wherein the inner catheter adapter is contained within the outer catheter adapter, the inner catheter is disposed within the outer catheter lumen, the inner catheter is movable with respect to the outer catheter between an inner catheter proximal position and an inner catheter distal position, and the inner catheter adapter is movable within the outer catheter adapter between an inner catheter adapter proximal position and an inner catheter adapter distal position, wherein the inner catheter adapter is slidable relative to the outer catheter adapter to move the inner catheter adapter and the inner catheter between the inner catheter adapter and inner catheter proximal positions and the inner catheter adapter and inner catheter distal positions; and a toggle joint comprising a distal end coupled to the outer catheter adapter and a proximal end coupled to the inner catheter adapter, wherein the toggle joint is in a raised position when the inner catheter adapter and the inner catheter are in the inner catheter adapter and inner catheter distal positions, and the toggle joint is in a flattened position when the inner catheter adapter and the inner catheter are in the inner catheter adapter and inner catheter proximal positions, and transitioning the toggle joint from the raised position to the flattened position moves the proximal end of the toggle joint away from the distal end of the toggle joint.

2. The catheter system of claim 1, wherein in response to the inner catheter being in the inner catheter distal position and the inner catheter adapter being in the inner catheter adapter distal position, the distal end of the inner catheter is disposed distal to the distal end of the outer catheter.

3. The catheter system of claim 1, further comprising a gap disposed between an outer surface of the inner catheter and the inner surface of the outer catheter, wherein when the inner catheter is in the inner catheter distal position and the inner catheter adapter is in the inner catheter adapter distal position, the inner catheter is disposed within the distal opening of the outer catheter and restricts flow distally into the gap, and in response to movement of the inner catheter from the inner catheter distal position to the inner catheter proximal position, the inner catheter is disposed proximal to the distal opening of the outer catheter and the gap is in fluid communication with the distal opening of the outer catheter.

4. The catheter system of claim 3, wherein a diameter of the outer catheter lumen tapers at the distal end of the outer catheter, such that the diameter of the outer catheter lumen at the distal end of the outer catheter is reduced.

5. The catheter system of claim 1, wherein the toggle joint is configured to depress to move the inner catheter and the inner catheter adapter to the inner catheter and inner catheter adapter proximal positions.

6. The catheter system of claim 1, wherein a plurality of fenestrations are disposed within the distal end of the inner catheter, and when the inner catheter adapter and the inner catheter are in the distal position, the plurality of fenestrations are disposed distal to the distal opening of the outer catheter.

7. The catheter system of claim 1, wherein a plurality of fenestrations are disposed within the outer catheter, and when the inner catheter adapter and the inner catheter are in the distal position, the distal end of the inner catheter is distal to the plurality of fenestrations.

8. The catheter system of claim 1, wherein the toggle joint comprises a groove, a crease, or a hinge between the distal end and the proximal end.

9. The catheter system of claim 1, wherein application of a depressing force on the toggle joint moves the toggle joint from the raised position to the flattened position, and upon removal of the depressing force, the toggle joint returns to the raised position.

10. The catheter system of claim 1, wherein application of a depressing force on the toggle joint moves the toggle joint from the raised position to the flattened position, and upon removal of the depressing force, the toggle joint stays in the flattened position.

11. The catheter system of claim 1, wherein the toggle joint is flexible.

12. The catheter system of claim 1, further comprising an extension tube in fluid communication with the inner catheter lumen, and extending through a slot in the outer catheter adapter.

13. The catheter system of claim 1, wherein at least one seal is disposed between the outer catheter adapter and the inner catheter adapter to seal a fluid path between the outer catheter adapter and the inner catheter adapter.

* * * * *